United States Patent [19]

Eggers et al.

[11] Patent Number: 4,998,933
[45] Date of Patent: Mar. 12, 1991

[54] THERMAL ANGIOPLASTY CATHETER AND METHOD

[75] Inventors: Philip E. Eggers, San Francisco; Hira V. Thapliyal, Mountain View, both of Calif.

[73] Assignee: Advanced Angioplasty Products, Inc., Mountain View, Calif.

[21] Appl. No.: 204,668

[22] Filed: Jun. 10, 1988

[51] Int. Cl.$^5$ .............................................. A61B 17/36
[52] U.S. Cl. ..................................... 606/41; 604/114; 606/31
[58] Field of Search ............ 128/303.1, 303.11–303.13, 128/341–344, 348.1, 419 P, 399–402, 786; 604/20, 96–103, 113, 114; 606/28, 31, 41, 194

[56] References Cited

U.S. PATENT DOCUMENTS

| | | | |
|---|---|---|---|
| 3,769,984 | 11/1973 | Muench | 128/786 |
| 4,038,519 | 7/1977 | Foucras | 604/114 |
| 4,660,571 | 4/1987 | Hess et al. | 128/303.1 |
| 4,699,157 | 10/1987 | Shonk | 128/786 |
| 4,709,698 | 12/1987 | Johnston et al. | 128/303.12 |
| 4,796,622 | 1/1989 | Lu et al. | 128/303.1 |
| 4,799,479 | 1/1989 | Spears | 606/28 |

FOREIGN PATENT DOCUMENTS 0182689 5/1986 European Pat. Off. .

OTHER PUBLICATIONS

Dotter, C. T. et al., "Transluminal Treatment of Arteriosclerotic Obstruction: Description of a New Technic and a Preliminary Report of Its Application," *Circulation* (1964), 30:654–670.

Grüntzig, A. R. et al., "Nonoperative Dilatation of Coronary-Artery Stenosis: Percutaneous Transluminal Coronary Angioplasty," *New England Journal of Medicine* (1979), 301:61–68.

Meier, B. et a., "Repeat Coronary Angioplasty", *Journal of American College of Cardiology* (1984), 4:463–466.

Cumberland, D. C. et al., "Percutaneous Laser Thermal Angioplasty: Initial Clinical Results with a Laser Probe in Total Peripheral Artery Occlusions," *Lancet* (Jun. 28, 1986), pp. 1457–1459.

Kensey et al., "Recanalization of Obstructed Arteries Using a Flexible Rotating Tip Catheter," *Abstracts of the 59th Scientific Sessions, Circulation* (1986), II-457.

Simpson, J. B. et al., "Transluminal Atherectomy: Initial Clinical Results in 27 Patients," *Abstracts of the 59th Scientific Sessions, Circulation* (1986), 74 II-203.

Simpson, J. B. et al., "Transluminal Coronary Atherectomy (TCA): Results in 21 Human Cadaver Vascular Segments," *Abstracts of the 59th Scientific Sessions, Circulation* (1986), 74 II-202.

Faxon, D. P. et al., "In Vivo Evaluation of Athrectomy, A New Technique to Enlarge Atherosclerotic Vessels," *Abstracts of the 58th Scientific Sessions Circulation* (1985), 72 III-469.

*Primary Examiner*—C. Fred Rosenbaum
*Assistant Examiner*—William W. Lewis
*Attorney, Agent, or Firm*—Townsend and Townsend

[57] ABSTRACT

This invention provides a method and apparatus for selectively heating an atheromatous mass which partially or fully occludes a particular blood vessel. As a result, the occlusive mass is effectively softened or weakened, allowing the occlusive mass to be more readily recanalized by expansion of a balloon or other dilitation means. This invention also provides a method and apparatus for effectively boring through a partially or fully occluded blood vessel by simultaneously applying both (1) heat to the occlusive mass surrounding the tip of the catheter and (2) pressure against the mass within the partially or fully occluded blood vessel.

6 Claims, 3 Drawing Sheets

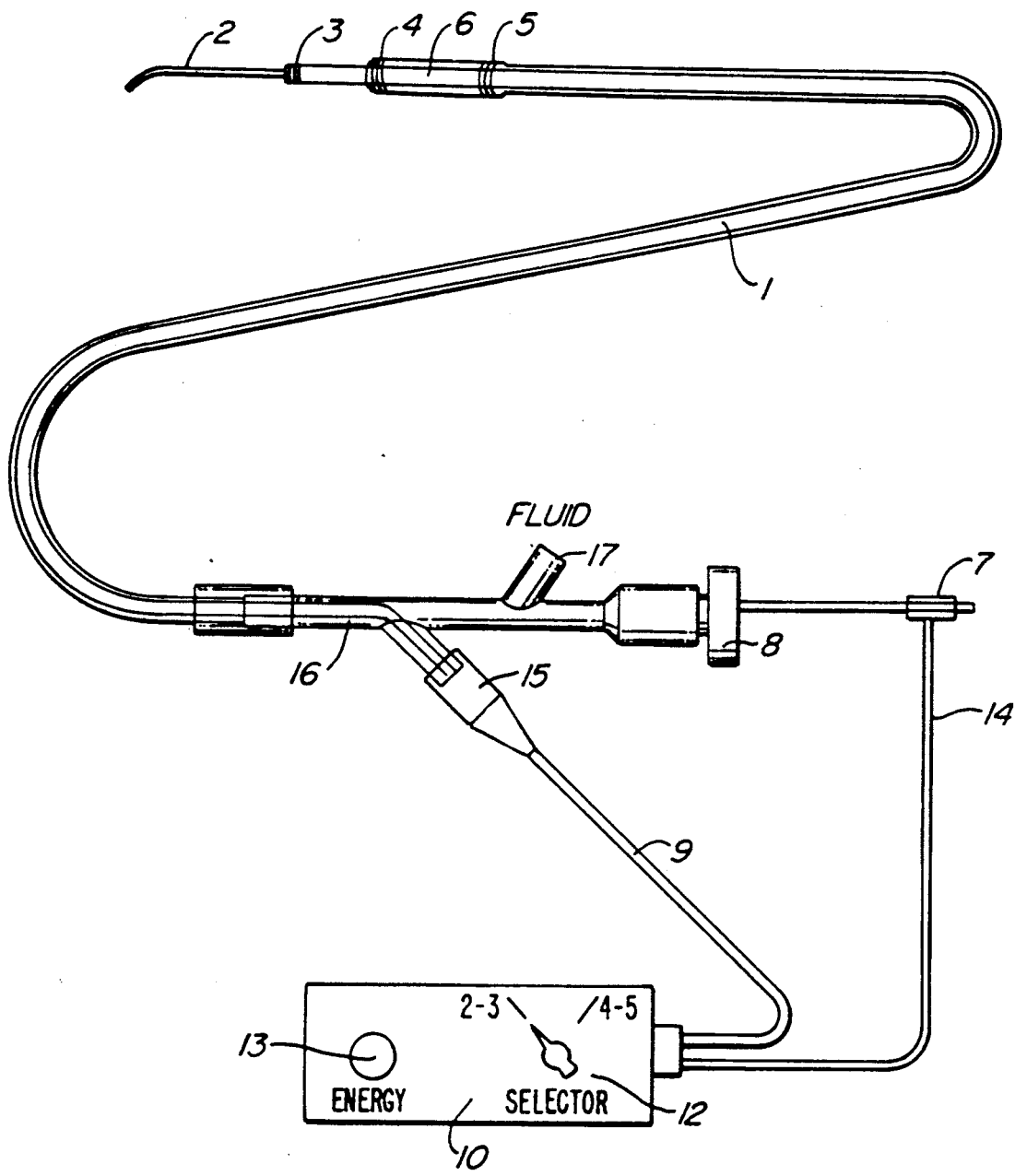
FIG._1.

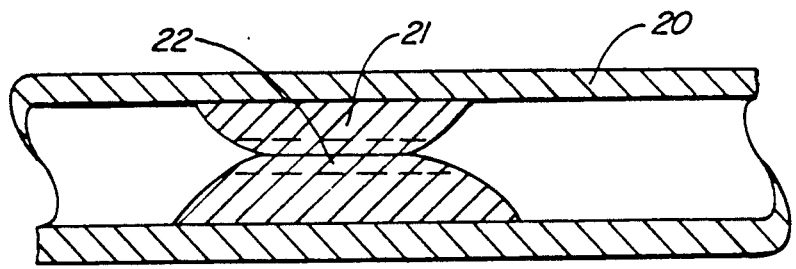
FIG._2.
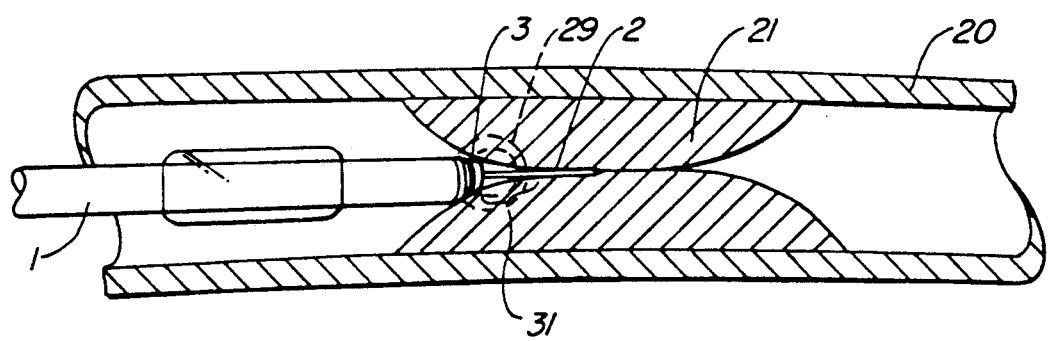
FIG._3.
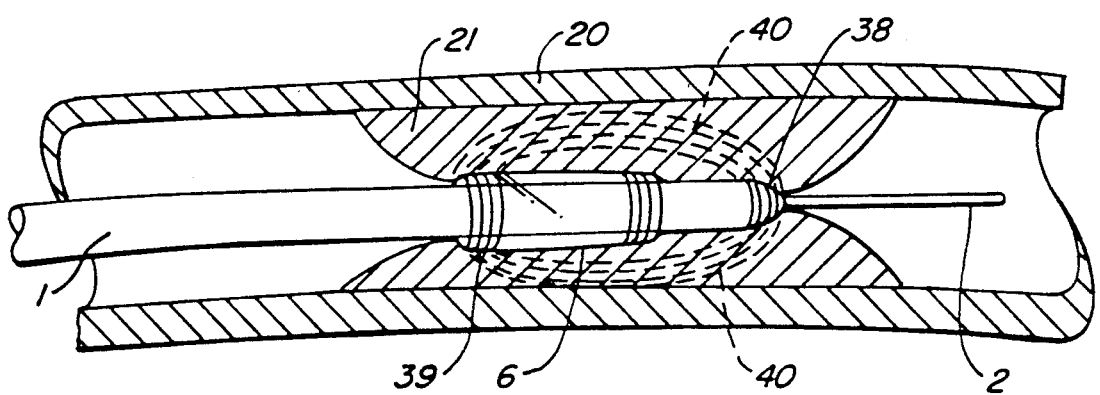
FIG._4.

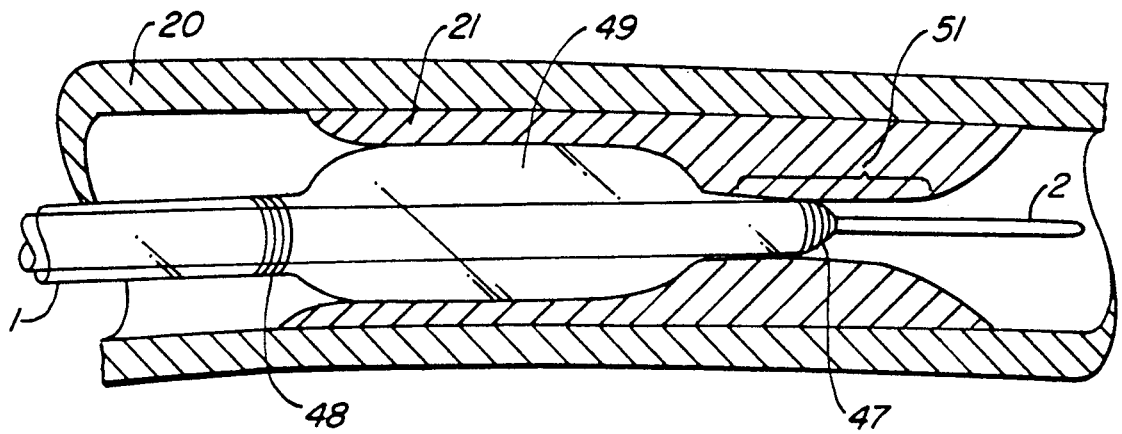
FIG._5.
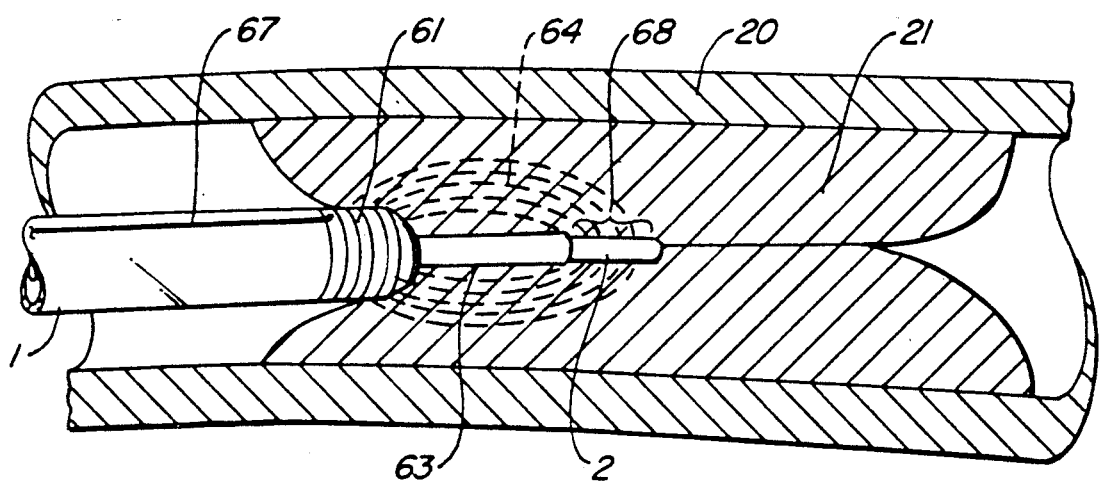
FIG._6.

THERMAL ANGIOPLASTY CATHETER AND METHOD

BACKGROUND OF THE INVENTION

1. Field of the Invention

This invention relates generally to catheters and in particular to a thermal angioplasty catheter.

2. Description of the Prior Art

Percutaneous transluminal balloon angioplasty (PTA) has become an established technique for treating atherosclerotic occlusive disease. The principle of intraluminal dilitation of arterial plaque was described by Dottėr in 1964. Dotter, C.T., et al., "Transluminal Treatment of Arteriosclerotic Obstruction: Description of a New Technique and a Preliminary Report of Its Application," *Circulation* (1964) 30:654. The treatment, however, was not widely accepted until the discovery of nonelastomeric balloons followed by the discovery of angiographic techniques for transluminal balloon angioplasty by Gruntzig in 1976. Gruntzig, R. A., et al., "Nonoperative Dilation of Coronary Artery Stenosis: Percutaneous Transluminal Coronary Angioplasty," *New England Journal of Medicine* (1979) 301:61.

The PTA technique utilizes a catheter that has a small diameter (typically 4 French to 8 French) and is equipped with an expandable chamber similar to a balloon. The chamber is concentric to the catheter and is located near the distal end of the catheter. The catheter is introduced into the appropriate blood vessel and is advanced through the vessel lumen to a narrowing of a blood vessel caused by atheromatous mass. The deflated balloon is positioned at the site of the atheromatous plaque. The balloon is inflated in a controlled manner by injection of an appropriate fluid, compacting the atheromatous mass. After the balloon is deflated, the blood vessel has a larger luminal diameter, thereby improving blood flow.

As a result of the high percentage of initially successful dilitations, transluminal balloon angioplasty has gained widespread acceptance. However, a significant recurrence rate of 30 percent, has been observed at the time of follow-up angiograms as reported by Meier and King. Meier, B., King, S., "Repeat Coronary Angioplasty," *Journal of American Colleqe of Cardioloov* (1984) 55:463. For this reason, other methods have been developed for the dilitation or removal of atheromatous plaque.

One method for the removal of atheromatous plaque utilizes a catheter incorporating an optical fiber for the transmission of laser energy to the distal portion of catheter and into the stenosed arteries. Using this technique, the stenosed arteries are recanalized by the application of laser energy to ablate or vaporize the atheromatous mass. One disadvantage of this method is the widespread thermal injury to the arterial wall resulting in arterial perforation, aneurysm formation and thrombosis. Another limitation of laser ablation methods is that calcified plaques cannot be vaporized but are often fragmented by acoustic shock waves created by the pulsed laser interaction with the plaque. When such fragmentation occurs, there is an increased potential for embolization.

An alternative method for recanalization of obstructed arteries has also been developed by Spears (see European Patent No. EP-85402067) and involves the filling of the balloon (used to expand the obstructed artery) with a liquid which has a high absorbance of laser light. The laser light is then transmitted to the balloon from an external laser source via a fiber optic within the angioplasty catheter. The liquid contained within the balloon is heated by the laser energy. This heating serves to minimize reclosure following conventional balloon angioplasty. Other methods of heating the fluid (e.g., water or water containing dye) in the balloon are also suggested by Spears including exothermic (chemical) reactions and resistance heating of fluid contained within the balloon.

Another method for supplying heat to the tip of the balloon angioplasty catheter has been suggested by Cumberland, et al. Cumberland, D.C., "Percutaneous Laser Thermal Angioplasty: Initial Clinical Results with a Laser Probe in Total Peripheral Artery Occlusions," *Lancet* (June 28, 1986) pp. 1457–1459. This technique utilizes a metal tip at the distal portion of the catheter. The metal tip is heated to about 400 C. by use of argon laser to recanalize occluded blood vessels.

Another method for recanalizing occluded blood vessels suggested by Kensey, et al., removes atheromatous plaque by using a rotating tip catheter to "drill" or bore through the occlusive mass. Kensey, et al., "Abstracts of the 59th Scientific Sessions, *Circulation* (1986) 74(II):11.

Another method of opening the stenosed blood vessel is described by Simpson, et al. Simpson J. B., et al., "Transluminal Atherectomy—Initial Clinical Results in 27 Patients," *Circulation* (Oct. 1986) 74 (II):4; "Transluminal Coronary Atherectomy (TCA), Results in 21 Human Cadaver Vascular Segments," *Circulation* (Oct. 1986) 74 (II):4; Faxon, D.P., et al., "In Vivo Evaluation of Atherectomy, A New Technique to Enlarge Atherosclerotic Vessels,"*Circulation* (Oct. 1985) 72 (II):4. In this method, a catheter device is used to cut and retrieve the occluding plaque from the artery. The catheter consists of a boat shaped metal housing, containing a high speed rotating cutter, and a balloon attached to the opposite side on the housing. The device is positioned at the site of the atherosclerotic narrowing in the artery, and the balloon is inflated to press the plaque into the opening of the housing. The rotating cutter is then advanced forward thereby cutting the atheroma which is protruding into the housing. The excised plaque is retrieved from the housing when the catheter is removed from the blood vessel. In this method, the lumen of the blood vessel is enlarged by cutting and removing the plaque which is occluding the blood flow. There are two main limitations of this method. First, the housing, made from a rigid material, can not be positioned safely in blood vessels at the site of a curve, as well as the sites of "high grade lesions" (i.e. small luminal openings). The second limitation of this device is that it removes the material in the longitudinal direction of the artery, creating a "channel" in the lumen. One has to create a number of these channels in the lumen circumferentially to more effectively treat the atherosclerotic disease in the artery.

SUMMARY OF THE INVENTION

This invention provides a method and apparatus for selectively heating an atheromatous mass which partially or fully occludes a particular blood vessel. As a result, the occlusive mass is effectively softened or weakened, allowing the occlusive mass to be more readily recanalized by expansion of a balloon or other dilitation means. This invention also provides a method and apparatus for effectively boring through a partially or fully occluded blood vessel by simultaneously applying both (1) heat to the occlusive mass surrounding the tip of the catheter and (2) pressure against the mass within the partially or fully occluded blood vessel.

This invention includes a means for guiding the catheter and the thermal heating means along a pathway approximating the central region of the occluded blood vessel. The guiding means is an electrically conducting wire that contains or serves as the first electrode of the heating means. The guiding means is extensible from the tip of the catheter and is located within and concentric to the catheter. A second electrode is provided proximal to the first electrode and positioned on or near the tip of the catheter. The application of high frequency voltage between these two electrodes results in the conduction of high frequency current and the generation of heat within the portion of the atheromatous mass located between the electrodes. The application of a preselected voltage between these two electrodes for appropriate intervals of time substantially weakens the atheromatous mass, allowing the catheter to penetrate and pass through the obstruction.

Once the partially or fully occluded blood vessel has been opened to allow passage of the catheter, the catheter can be advanced to position an expansion means within the length of the occlusive mass. The expansion means is bridged by a third and fourth electrodes. The expansion means is utilized for subsequent inflation and dilitation of the atheromatous mass. When the third and fourth electrodes are energized by a controlled high frequency voltage level, heating occurs within the atheromatous mass surrounding the expansion means. This heat weakens the mass to facilitate dilitation of the mass by the expansion means.

Direct heating of the atheromatous mass by conduction of a high frequency current weakens the mass over a distributed region. The use of a high frequency current for heating also minimizes induced stimulation of muscle tissue or nerve tissue in the vicinity of the tissue being heated. In addition, high frequencies minimize the risk of interfering with the natural pacing of the heart in circumstances where the thermal angioplasty catheter of the present invention is used in close proximity to the heart.

In contrast, surface heating methods in which a heating element is disposed on the surface of the catheter and the element is heated to an elevated temperature, are limited for the following reasons. First, direct heating methods are limited by conduction heat transfer through the mass. The surface immediately adjacent to and in contact with the heating element is exposed to substantially higher temperatures than regions further away as a consequence of the lower thermal conductivity of said atheromatous mass. Second, direct heating methods are limited by the presence of any residue which accumulates on the surface of the heating element. The residue acts as a thermal insulating layer, impeding the transfer of heat from the heating element to the surrounding atheromatous mass.

A further advantage of the present invention is that the heating means can be adapted to a wide range of catheter sizes appropriate to the particular size of the occluded blood vessel being recanalized, typically in the range of diameters from 0.05 to 0.150 inches. The present invention also incorporates a guidewire which can function as both a means for controlling the path of the angioplasty catheter and to concentrate the thermal power density dissipated directly into the atheromatous mass by serving as the tip electrode.

The energy source of the present invention includes the capability to deliver a high frequency current at power levels ranging from several watts to 50 watts, depending on the size of the atheromatous mass being heated, the size of the blood vessel being recanalized, and the duration of the energy pulse applied. The energy source allows the user to select the power level, pulse duration and number of energy pulses to be applied, according to the specific requirements of a particular angioplasty procedure. The user also selects which region of the catheter is to be energized depending upon the particular situation.

BRIEF DESCRIPTION OF THE DRAWINGS

FIG. 1 is a perspective view of a preferred embodiment of the thermal angioplasty catheter;

FIG. 2 is a cross-sectional view of a typical vascular occlusion prior to recanalization;

FIG. 3 is a cross-sectional view of the application of a preferred embodiment of the invention to a vascular occlusion by using the tip electrodes to penetrate through the atheromatous mass;

FIGS. 4 and 5 are cross-sectional views of the application of a preferred embodiment of the invention to a typical vascular occlusion by using the electrodes and expansion means to heat and expand the atheromatous mass; and FIG. 6 is a cross-sectional view of the heating electrodes at the tip of the catheter.

DETAILED DESCRIPTION OF THE PREFERRED EMBODIMENTS

In the preferred embodiment shown in FIG. 1, the thermal angioplasty catheter 1 includes a guidewire 2, which functions both as a means for guiding the catheter into the proper position and as an electrode. The entire guidewire may be an electrode or the guidewire may contain an electrode. The catheter also includes an electrode 3, disposed on the tip of the catheter 1 and electrically insulated from the guidewire electrode 2. The pair of electrodes 2 and 3 provide a means for applying a source of high frequency current to the atheromatous mass in situations in the blood vessel which is fully occluded or where the pathway is too small to allow passage of the thermal angioplasty catheter 1.

The thermal angioplasty catheter 1 also includes a second set of electrodes consisting of electrode 4 and electrode 5, electrically insulated from each other and from the first set of electrodes 2 and 3. The second set of electrodes 4 and 5 are disposed on or near the surface of the thermal angioplasty catheter 1, and the outside diameter of the electrodes 4 and 5 is comparable to the diameter of the thermal angioplasty catheter 1 to accommodate electrical contact with the atheromatous mass. The second set of electrodes 4 and 5 are disposed at either end of an expansion means 6, which can be inflated or otherwise expanded to accomplish an increase in the inner diameter of the partially occluded blood vessel. In use, the heat provided by electrodes 4 and 5 thermally weakens the atheromatous mass, thereby increasing the effectiveness of the recanalization procedure. The electrodes 4 and 5 may also be disposed, in part or whole, on the surface of, and at either end of, the expansion means 6. This allows the expansion means 6, when inflated or enlarged, to ensure good electrical contact between said electrodes 4 and 5 and the atheromatous mass to be heated and dilated.

The first set of electrodes 2 and 3 are in electrical communication with a source 10 of high frequency current through electrically conducting leads 16. The leads 16 are joined to an external cable 9 by a removable connector 15. In the embodiment of the invention shown in FIG. 1, the guidewire 2 may serve as one of the electrical leads if it is an electrically conducting material such as stainless steel. The source 10 is electrically connected to the guidewire 2 through an external lead 14 and connector 7.

The second set of electrodes 4 and 5 are in electrical communication with the source 10 of high frequency current through electrically conducting leads 16. The leads 16 are joined to an external cable 9 by a removable connector 15. The source 10 of high frequency current includes a means 13 for controlling the amount of energy applied to either set of electrodes 2 and 3 or 4 and 5. The source 10 of high frequency current also includes a control 12 for selecting which set of electrodes 2 and 3, or 4 and 5, is energized.

In the embodiment shown in FIG. 1, the expansion means 6 may be activated by use of a pressurizing fluid introduced in a controlled manner through external fluid port 17. The position of said guidewire 2 relative to catheter 1 may be secured by use of manually actuated locking means 8.

To facilitate the description of the preferred embodiment of this invention, a cross-sectional view of an occluded blood vessel is illustrated in FIG. 2. In the most severe cases of occluded blood vessels (known as total occlusions), the blood vessel 20 is totally occluded by an atheromatous mass 21. In less severe cases of occluded blood vessels, known as partially occluded blood vessels, the central region 22 of the atheromatous mass 21 is open, allowing a limited flow of blood.

FIG. 3 illustrates how the preferred embodiment of the invention can be applied to blood vessels partially or totally occluded with an atheromatous mass 21. In this case, the guidewire 2 is advanced to the site of the occlusion 21, then the catheter 1 is advanced along the guidewire 2 until it reaches the site of the occlusion 21. Next, the guidewire 2 is advanced beyond the tip of the catheter 1 to provide an exposed length 31 of the guidewire 2. This extension 31 of the guidewire 2 may be maintained by an enlarged guidewire diameter or mechanical "stop" which serves to prevent the guidewire 2 from completely receding into the catheter 1 while assuring a minimum exposed length 31 of guidewire 2 beyond the catheter 1.

Once the catheter 1 and guidewire 2 are in contact with the atheromatous mass 21 at the site of the occlusion, the two electrodes 2 and 3 are energized, causing current to flow between electrodes 2 and 3 along pathways or current flux lines 29. Because of the electrical resistance of the atheromatous mass 21, the localized current flow 29 causes the atheromatous mass 21 to be heated within the envelope of the current flux lines 29. The localized heating of the mass 21 is adjusted by varying the intensity and duration of the high frequency current.

Once a sufficient temperature rise is accomplished, the mechanical strength of the mass is substantially reduced in a localized region surrounding the tip of the catheter 1. This allows the catheter 1 and guidewire 2 to be advanced incrementally through the mass 21 by applying pressure on the portions of the catheter 1 and guidewire 2 external to the patient. This pressure is transmitted along the length of the catheter 1 to the tip region of the catheter to create a load or "boring pressure" sufficient to penetrate mass 21.

The method of controlling the heating by the thermal angioplasty catheter of this invention can be accomplished by other means. However, it is advantageous in many applications of the present invention to control the amount of energy delivered, selected according to the approximate size of the blood vessel being recanalized. For example, the recanalization of a blood vessel with an interior nominal diameter of 0.15 inch will require more energy (i.e., calories of heat input) than the recanalization of a blood vessel having a nominal inside diameter of 0.075 inches. This is due to the difference in the mass of the occlusion to be heated to the elevated temperature range required to weaken the structure of the atheromatous mass. Accordingly, the invention will be described as a heating means whereby the amount of energy delivered is controlled and is preselected by the user, according to the size of the blood vessel being recanalized.

Although the method of dilitation used to increase the inner diameter of the lumen by compressing the atheromatous mass can be accomplished by other means to achieve patency of blood vessels being recanalized, it is advantageous in many applications of the present invention to utilize an expandable means disposed on the catheter between one set of electrodes located proximal to the tip of said catheter.

This invention also can be utilized for a partially occluded blood vessel in which the diameter of the pathway for blood flow through the atheromatous mass 21 is smaller than the outside diameter of the catheter 1. In this situation, the invention can be used to enlarge the pathway sufficiently to allow passage of the catheter 1, thereby accommodating the subsequent dilitation of the atheromatous mass 21 with the combined use of heat and expansion described more fully in FIG. 4.

FIG. 4 illustrates how a second preferred embodiment of the invention can be applied to partially occluded blood vessels. In the embodiment of this invention shown in FIG. 4, the blood vessel 20 is partially occluded with an atheromatous mass 21, having a pathway with a diameter sufficiently large to allow the passage of the catheter 1. The catheter 1 is advanced to the site of the occlusion and is positioned, using radiographic imaging or other means, so that the electrodes 38 and 39 are located within the length of the atheromatous mass 21. Once the catheter 1 and, more particularly, electrodes 38 and 39 are in contact with the atheromatous mass 21, the two electrodes 38 and 39 are energized, causing current to flow along flux lines 40. Because of its electrical resistance, current flow 40 in the mass 21 heats the mass 21 in the region defined within the envelope of the current flux lines 40. Heating of the mass 21 in the vicinity of electrodes 38 and 39 may be varied by adjusting the intensity and duration of current flow. The expansion means 6 is then inflated with fluid, compressing the weakened atheromatous mass. The expansion means is designed to withstand the application of up to 12 atmospheres of pressure. In addition, the expansion means must be able to withstand the exposure to the heated atheromatous mass. Following the dilitation of a region of atheromatous mass 21, the catheter 1 may be repositioned so that the remaining portions of the occluded blood vessel can be heated and simultaneously dilated to restore the patency of the blood vessel 20.

The embodiment of the present invention illustrated in FIG. 4 differs from that illustrated in FIG. 1 in that only three electrodes and associated leads are required in place of the four electrodes illustrated in FIG. 1. The three-electrode embodiment allows the tip electrode 38 to be used either with the proximal electrode 39 or in conjunction with the guidewire/electrode 2.

FIG. 5 illustrates how the present invention is used to expand the mass 21 immediately following heating in accordance with FIG. 4. After the mass 21 is heated to a predetermined temperature range either as measured by a temperature sensing means disposed within said thermal angioplasty catheter 1, the expansion means 6 is inflated. The temperature sensing may be achieved using fiber optics with infrared sensing techniques, a thermocouple a thermistor or other temperature measurement means, or it may be predetermined by introducing a predetermined quantity of energy in accordance with the approximate size of the blood vessel being recanalized. The expansion compresses the heated mass 21, resulting in a localized increase in the interior diameter of the blood vessel. As shown in FIG. 5, the dilitation of the occluded blood vessel 20 may affect only a portion of the total length of said atheromatous mass 21. Accordingly, following the heating and dilitation process, catheter 1 may be repositioned such that the electrodes 47 and 48 are on either side of the next section 51 of the mass 21 to be dilated. The process of heating and dilitation can be repeated until the full length of the obstructed blood vessel 20 is dilitated and patency of said blood vessel 20 is restored.

FIG. 6 further illustrates a detailed cross-sectional view of the catheter for use in the penetration of partially or fully occluded blood vessels. The distal end of catheter 1 is shown in contact with atheromatous mass 21 with guidewire/electrode 20 inserted into said atheromatous mass within blood vessel 20. A second electrode 61 is disposed at the distal end of catheter 1. Catheter 1 is composed of an insulating material so that the application of a high frequency voltage to the electrodes 2 and 61 will result in current flow lines 64 in the atheromatous mass 21. Guidewire/electrode 2 is covered with an electrically insulated layer 63 except for the tip region 68. The tip region allows the flow of current 64 between electrodes 2 and 61. Electrode 61 is connected to an external source of power by an electrical connection means 67. The electrical connection means is electrically insulated from guidewire/electrode 2 over the entire length of the catheter.

While the above description provides a full and complete disclosure of the preferred embodiment of the invention, various modifications, alternative constructions, and equivalents may be employed. For example, the power could be communicated to the electrodes by wires embedded in the catheter wall. Also, a series of electrodes could be employed with multiple expansion means to "caterpillar" through an occluded blood vessel. Accordingly, the above description and illustration should not be construed as limiting the scope of the invention, which is defined by the appended claims.

What is claimed is:

1. In an angioplasty catheter having a dilation means, the improvement comprising:
   a first electrode located on an extensible guidewire;
   second electrode located at a distal end of said catheter electrically insulated from said first electrode;
   a third electrode located at a distal end of said dilation means electrically insulated from said first and second electrodes;
   a fourth electrode located at a proximal end of said dilation means electrically insulated from said first, second, and third electrodes;
   whereby said guidewire comprises said first electrode;
   whereby said second, third, and fourth electrodes are annular metallic regions having a wire extending therefrom;
   means for selectively communicating an electric current to said electrodes to thereby cause heating of a resistive mass located between said electrodes;
   whereby said means for communicating an electric current to said second, third, and fourth electrodes comprises at least one wire contained within the catheter; and
   whereby said guidewire comprises said means for communicating an electric current to said first electrode.

2. A method of boring through an arteriosclerotic obstruction or a portion thereof, the method comprising the steps of:
   positioning a first electrode on a guidewire of a catheter against said obstruction;
   inserting a second electrode into or through said obstruction;
   conducting a high frequency current between said electrodes through said obstruction; and
   exerting pressure against said obstruction.

3. A catheter comprising:
   a catheter member;
   dilitation means affixed to the catheter member;
   a guidewire extending through the catheter member;
   a first electrode affixed to the guidewire;
   a second electrode affixed to the catheter member and electrically isolated from the first electrode;
   means for selectively communicating an electric current to the first and the second electrodes to thereby cause heating of a resistive mass therebetween;
   a third electrode affixed to the catheter at a distal end of the dilitation means, the third electrode insulated from each of the first and the second electrodes;
   a fourth electrode affixed to the catheter at a proximal end of the dilitation means, the fourth electrode electrically insulated from each of the first, second and third electrodes; and
   means for selectively communicating an electric current to the third and fourth electrodes to thereby cause heating of a resistive mass therebetween.

4. A catheter as in claim 3 wherein the third electrode extends annularly around a circumferential portion of the catheter member; and
   the fourth electrode extends annularly around a circumferential portion of the catheter member.

5. A catheter comprising:
   at least four electrodes located on the catheter electrically insulated from each other, wherein the first and second electrodes extend circumferentially in an annular band around the periphery of the catheter, the first electrode is affixed to a guidewire extending through the catheter, the third electrode is affixed to the catheter at a distal end of a dilitation means, and the fourth electrode is affixed to the catheter at a proximal end of the dilitation means, and the catheter further comprising;

a means for selectively communicating an electric current to the first and second electrodes to thereby cause heating of a resistive mass therebetween;
a means for selectively communicating an electric current to the third and the fourth electrodes to thereby cause heating of a resistive mass therebetween; and
a temperature-sensing means disposed proximate a distal end of the catheter for sensing temperature of regions surrounding the distal end of the catheter.

6. An angioplasty catheter comprising:
a catheter member;
dilation means affixed to the catheter member;
a guidewire extending through the catheter member;
a first electrode affixed to the guidewire;
a second electrode affixed to the catheter member and electrically isolated from the first electrode;
a third electrode affixed to the catheter member at a distal end of the dilation means, the third electrode insulated from each of the first and the second electrodes;
a fourth electrode affixed to the catheter at a proximal end of the dilation means, the fourth electrode insulated from each of the first, second and third electrodes; and
means for selectively communicating an electric current to the first, second, third, and fourth electrodes to thereby cause heating of a resistive means disposed in proximity to the electrodes.

* * * * *